US010881938B2

(12) United States Patent
Lim et al.

(10) Patent No.: US 10,881,938 B2
(45) Date of Patent: Jan. 5, 2021

(54) DEVICE FOR ANALYZING ATHLETIC POSTURE AND METHOD FOR GENERATING ANALYZING INFORMATION FOR ATHLETIC POSTURE

(71) Applicant: GOLFZON CO., LTD., Daejeon (KR)

(72) Inventors: Kang Yoon Lim, Daejeon (KR); Mi Sun Lee, Daejeon (KR); Heung Ryul Zo, Daejeon (KR)

(73) Assignee: GOLFZON CO., LTD., Daejeon (KR)

( * ) Notice: Subject to any disclaimer, the term of this patent is extended or adjusted under 35 U.S.C. 154(b) by 746 days.

(21) Appl. No.: 15/503,401

(22) PCT Filed: Aug. 12, 2015

(86) PCT No.: PCT/KR2015/008456
§ 371 (c)(1),
(2) Date: Feb. 12, 2017

(87) PCT Pub. No.: WO2016/024817
PCT Pub. Date: Feb. 18, 2016

(65) Prior Publication Data
US 2017/0225054 A1    Aug. 10, 2017

(30) Foreign Application Priority Data
Aug. 12, 2014 (KR) .................. 10-2014-0104222

(51) Int. Cl.
*A63B 69/36* (2006.01)
*A61B 5/11* (2006.01)
(Continued)

(52) U.S. Cl.
CPC ........ *A63B 69/3667* (2013.01); *A61B 5/1036* (2013.01); *A61B 5/1116* (2013.01);
(Continued)

(58) Field of Classification Search
CPC ................................................ A63B 69/3667
See application file for complete search history.

(56) References Cited

U.S. PATENT DOCUMENTS 5,118,112 A * 6/1992 Bregman ........... A63B 24/0021
434/252
5,372,365 A * 12/1994 McTeigue .......... A63B 24/0003
434/252
(Continued)

FOREIGN PATENT DOCUMENTS

JP       07-231968 A     9/1995
JP      2003-038462 A    2/2003
(Continued)

OTHER PUBLICATIONS

International Search Report for PCT/KR2015/008456 dated Nov. 16, 2015 from Korean Intellectual Property Office.

*Primary Examiner* — Xuan M Thai
*Assistant Examiner* — Sadaruz Zaman
(74) *Attorney, Agent, or Firm* — Revolution IP, PLLC

(57) ABSTRACT

Disclosed is an athletic posture analysis device for analyzing an athletic posture taken by a user who stands on a foot plate, the athletic posture analysis device comprising: a pressure sensor plate provided at the foot plate for measuring a distribution of pressure applied to each of feet of the user, who performs an athletic action, by a weight of the user; a display device for displaying athletic posture analysis information of the user; and a controller for performing control so as to display a predetermined foot image and information regarding the distribution of pressure applied to each of the feet of the user in an overlapping fashion through the display device and to track a position of each of the feet of the user changed according to the user's athletic action and display the foot image.

9 Claims, 16 Drawing Sheets

(a)

(b)

(51) Int. Cl.
*A61B 5/103* (2006.01)
*A63B 71/06* (2006.01)

(52) U.S. Cl.
CPC ...... *A63B 71/0622* (2013.01); *A61B 2503/10* (2013.01); *A63B 2069/367* (2013.01); *A63B 2220/56* (2013.01)

(56) References Cited

U.S. PATENT DOCUMENTS

| | | | | |
|---|---|---|---|---|
| 5,605,462 | A | * | 2/1997 | Denne ................. F15B 15/00 434/372 |
| 5,885,229 | A | * | 3/1999 | Yamato ............... A61B 5/1038 600/587 |
| 5,919,045 | A | * | 7/1999 | Tagge ................. A63F 13/08 434/29 |
| 7,335,117 | B2 | | 2/2008 | Reason-Kerkhoff |
| 7,946,928 | B2 | * | 5/2011 | Mooney ............ A63B 69/3667 473/269 |
| 2004/0209698 | A1 | * | 10/2004 | Ueda ................. G06T 1/0007 473/150 |
| 2008/0242437 | A1 | * | 10/2008 | Taylor ............... A63B 24/0021 473/269 |
| 2014/0156040 | A1 | * | 6/2014 | Mooney ............... A63B 69/36 700/91 |
| 2017/0189784 | A1 | * | 7/2017 | Sasaki ............... A63B 69/3608 |

FOREIGN PATENT DOCUMENTS

| | | | |
|---|---|---|---|
| KR | 10-2002-0023720 | A | 3/2002 |
| KR | 10-2003-0065778 | A | 8/2003 |
| KR | 10-0393352 | B1 | 8/2003 |
| KR | 10-2007-0013395 | A | 1/2007 |
| KR | 10-1458931 | B1 | 11/2014 |

\* cited by examiner

[Fig. 2]

FIG. 3
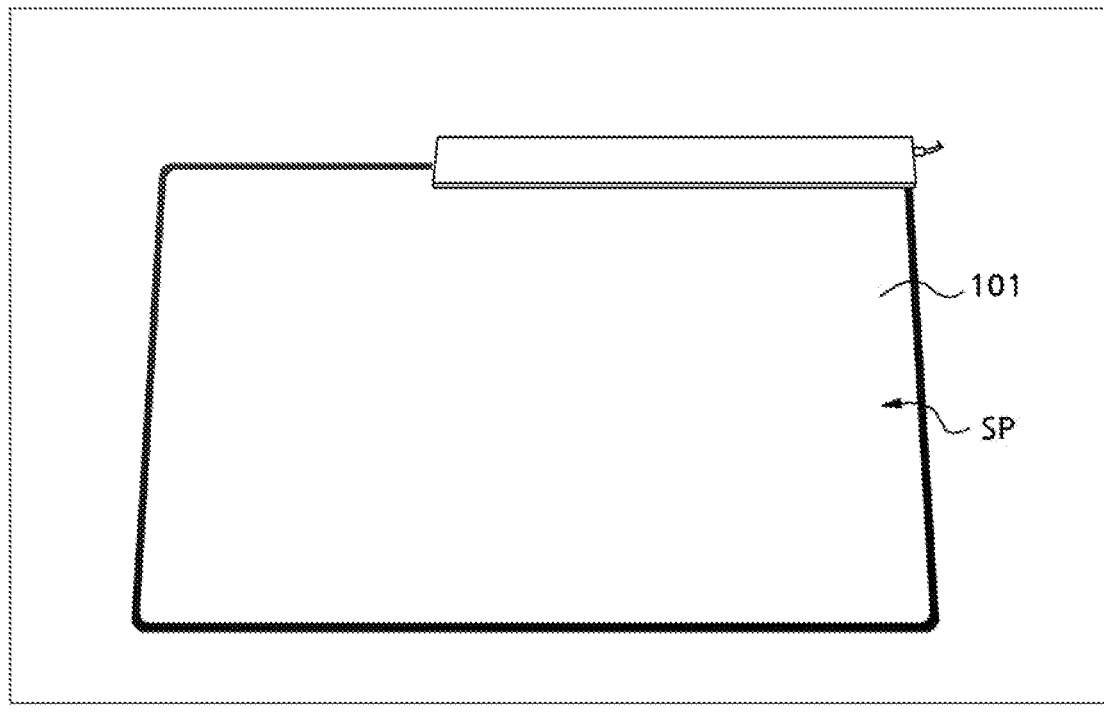
(a)
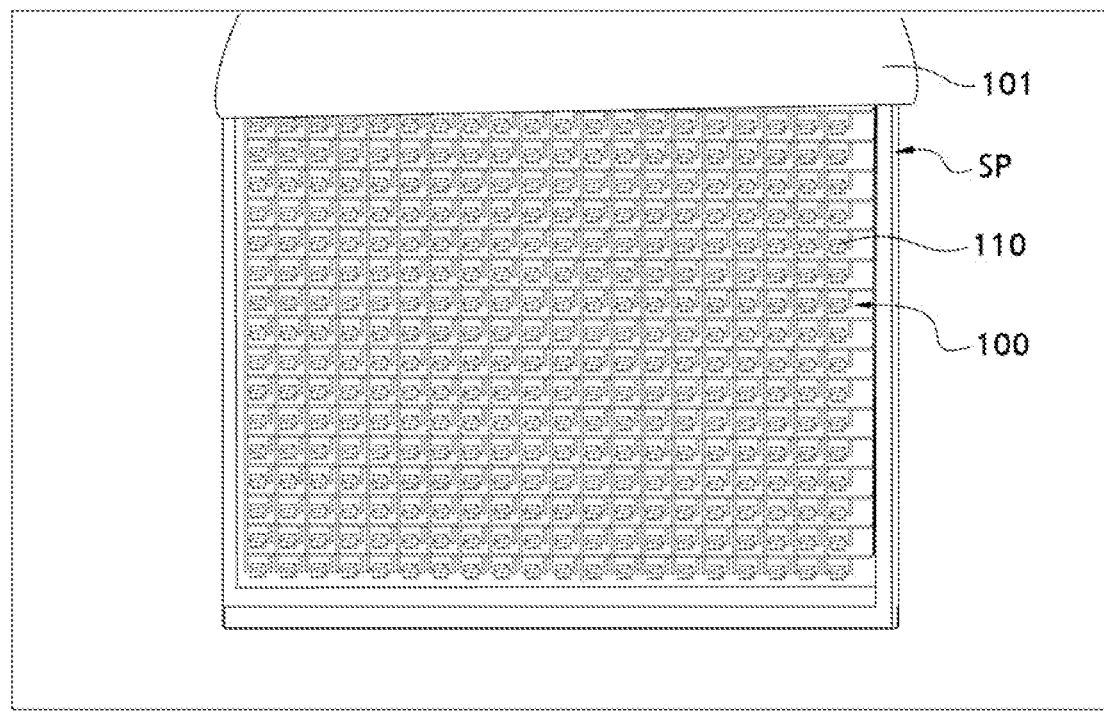
(b)

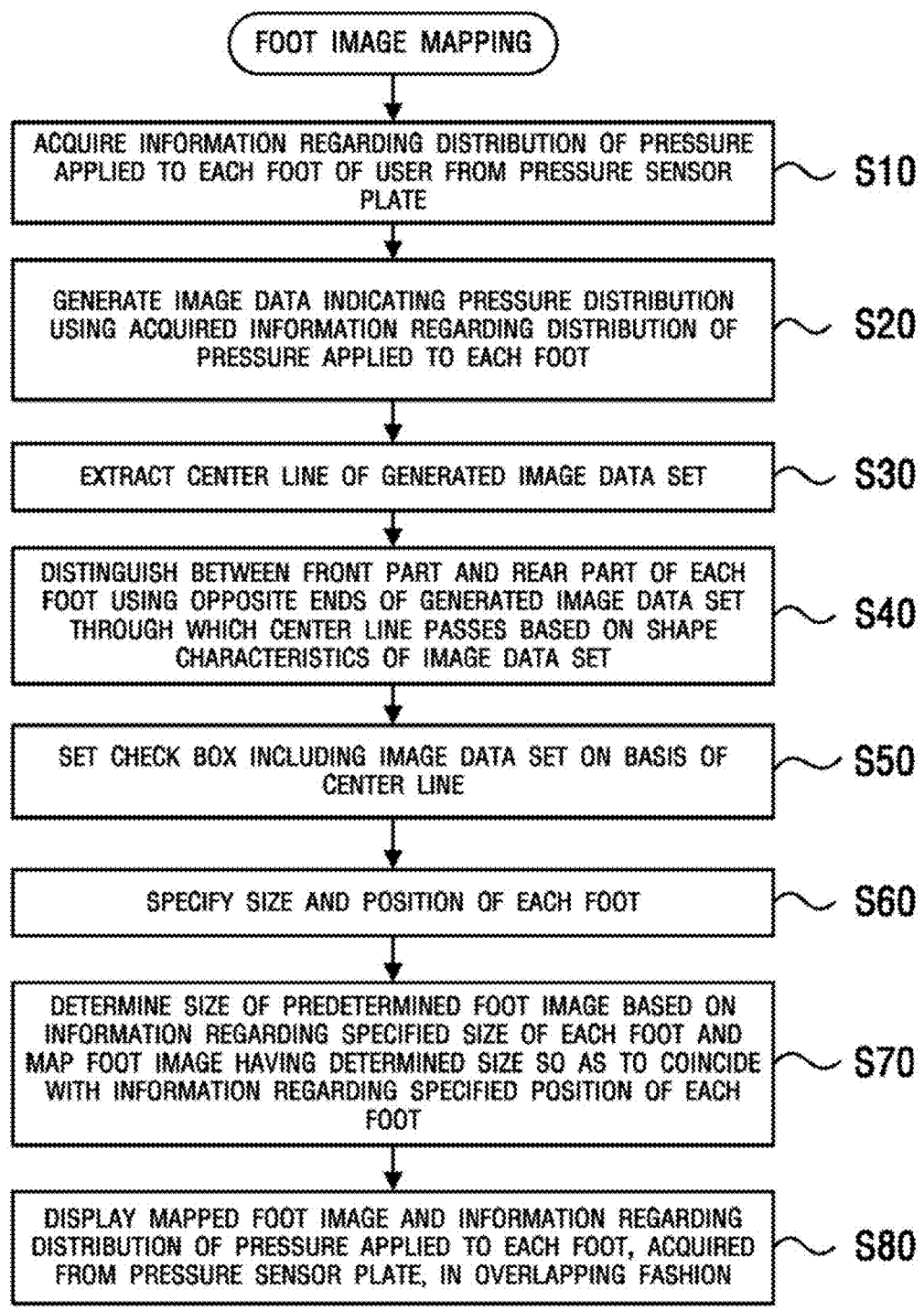

[Fig. 5]
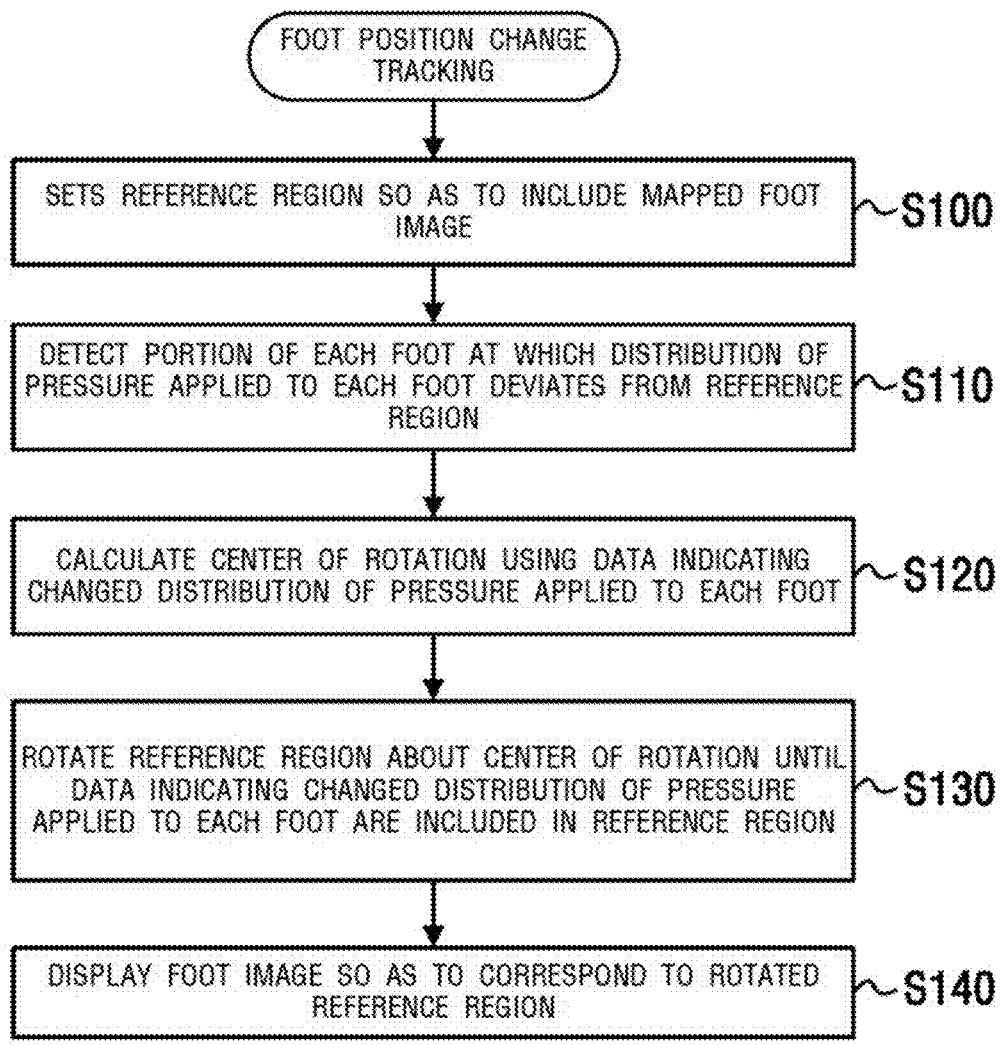

[Fig. 6]
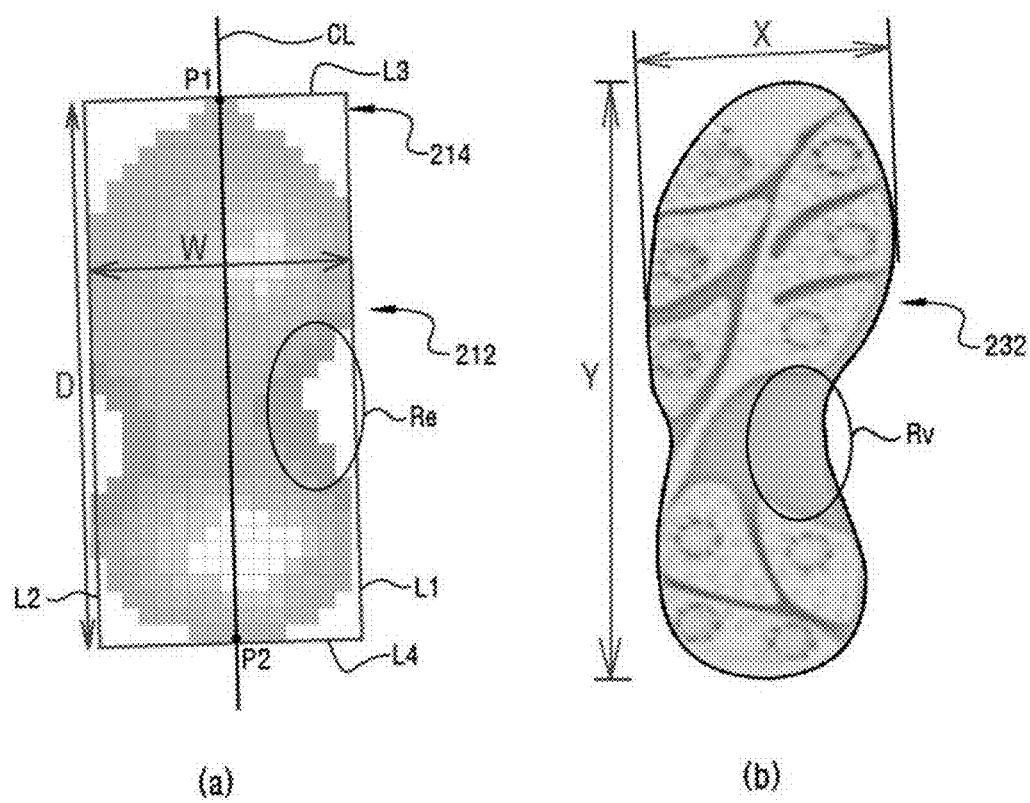
(a)  (b)

[Fig. 7]
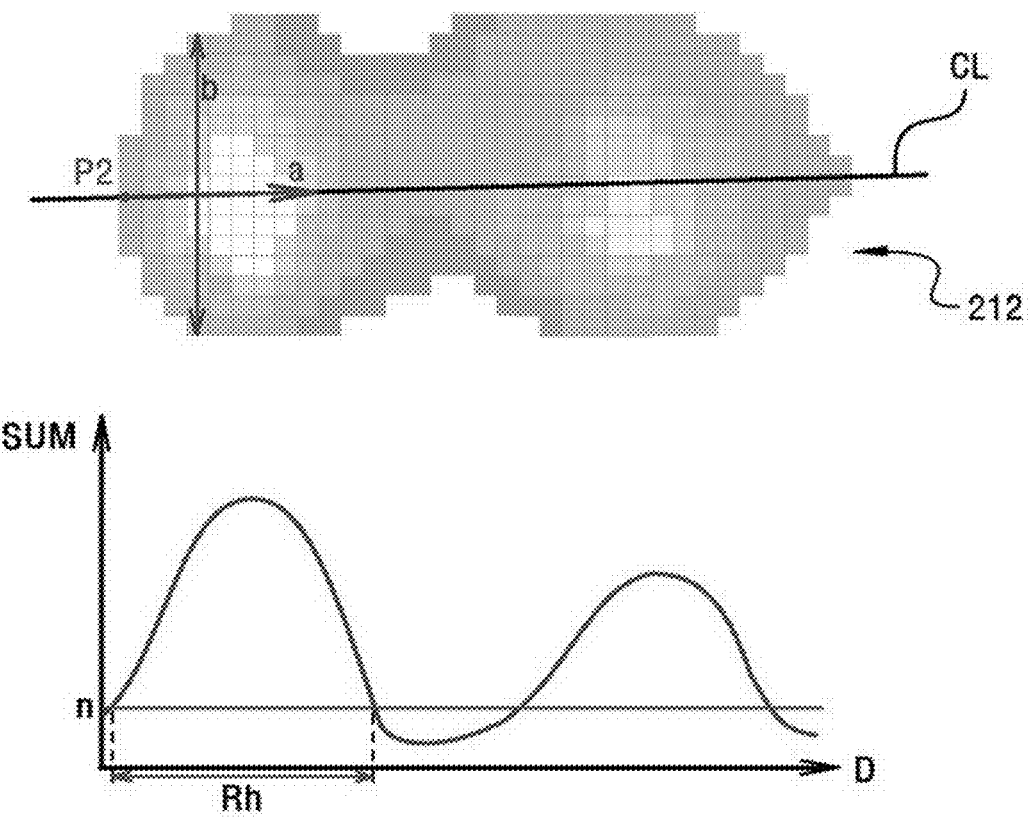

[Fig. 8]
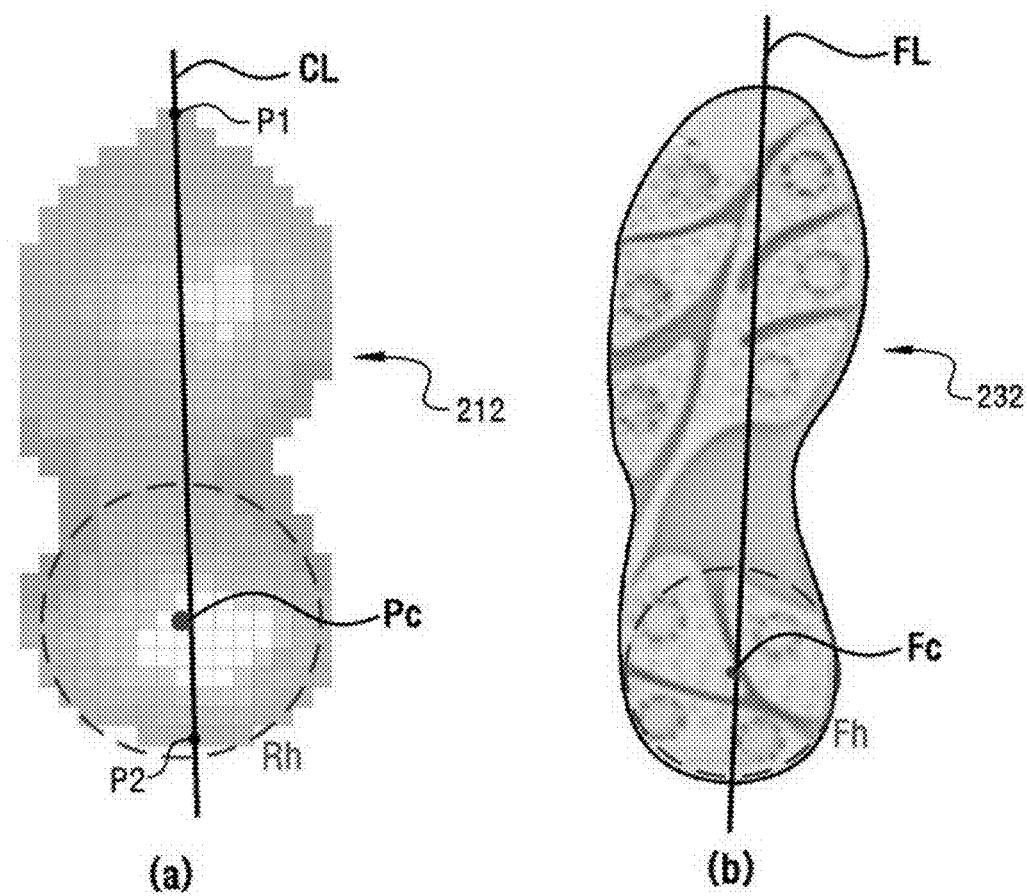
(a)          (b)

[Fig. 9]
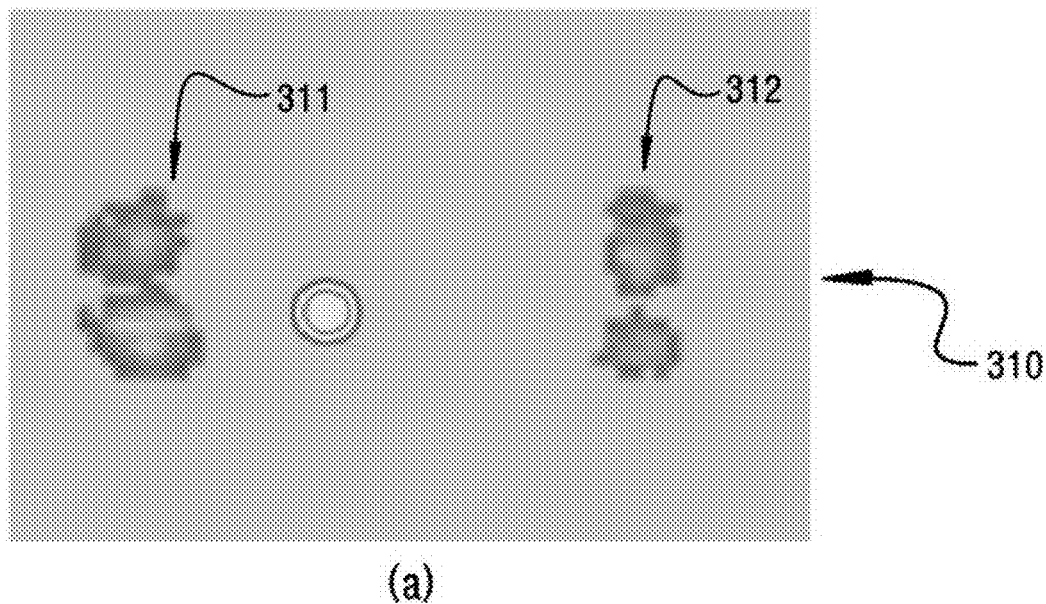
(a)
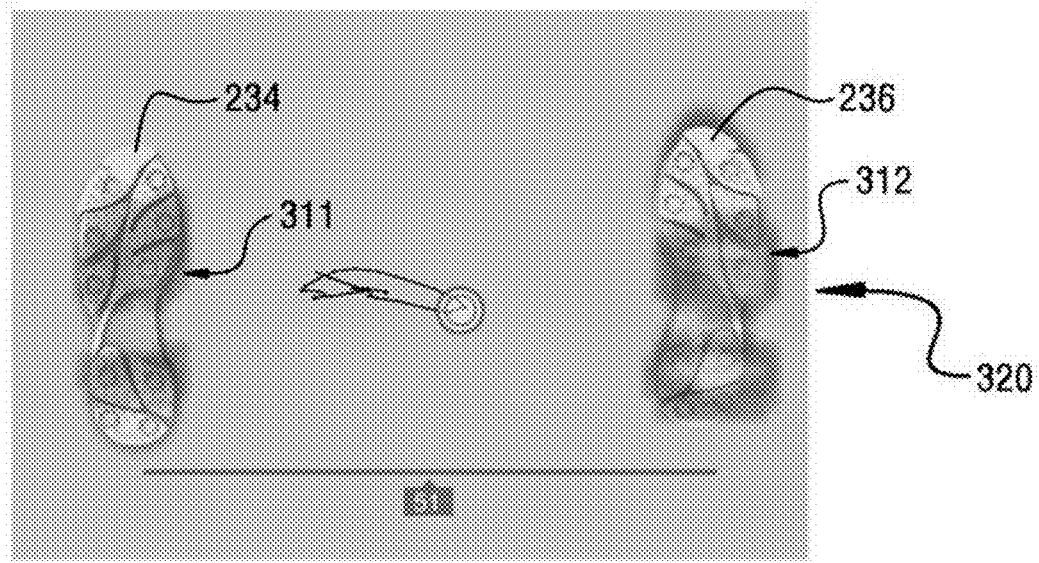
(b)

【Fig. 10】
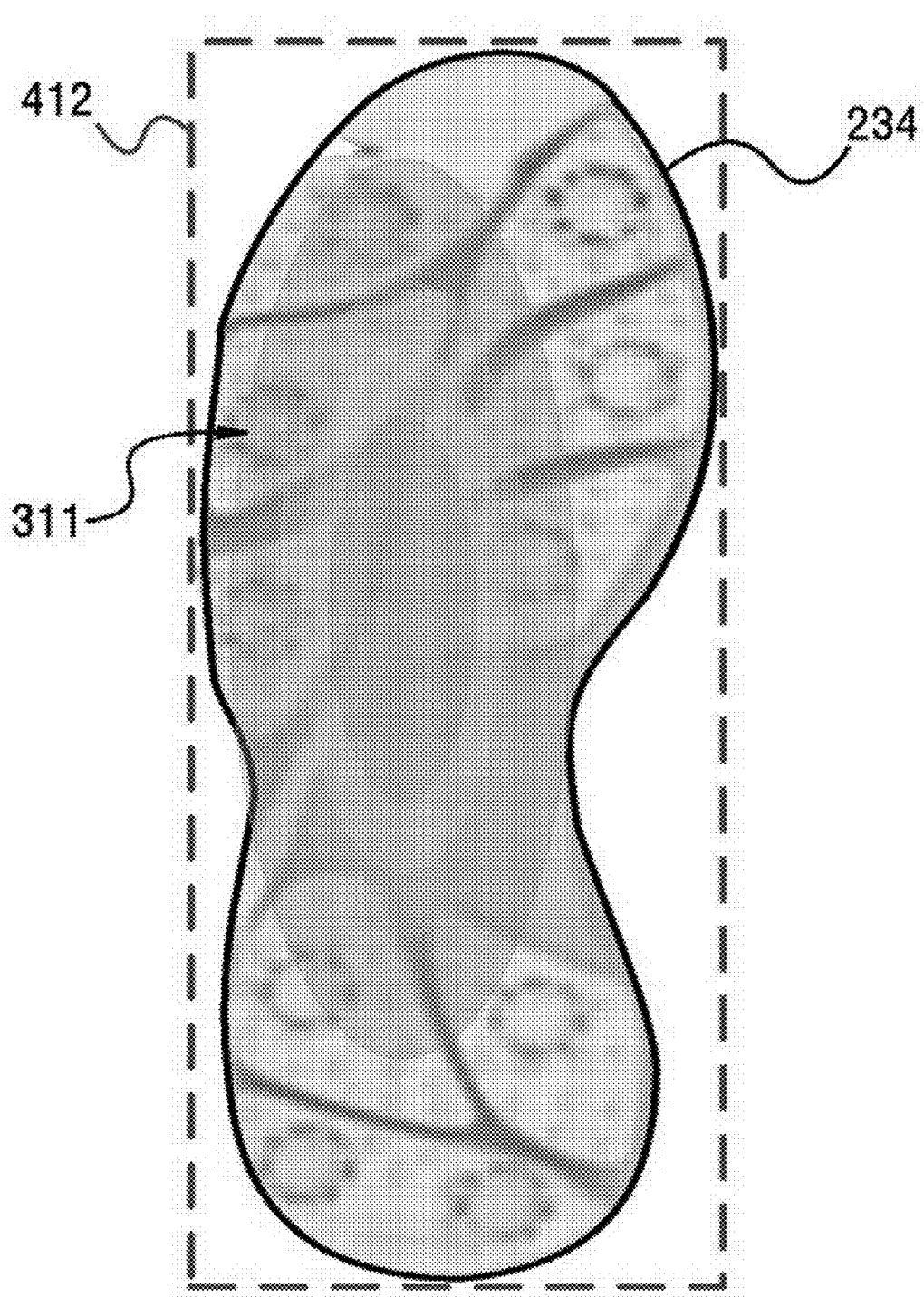

【Fig. 11】
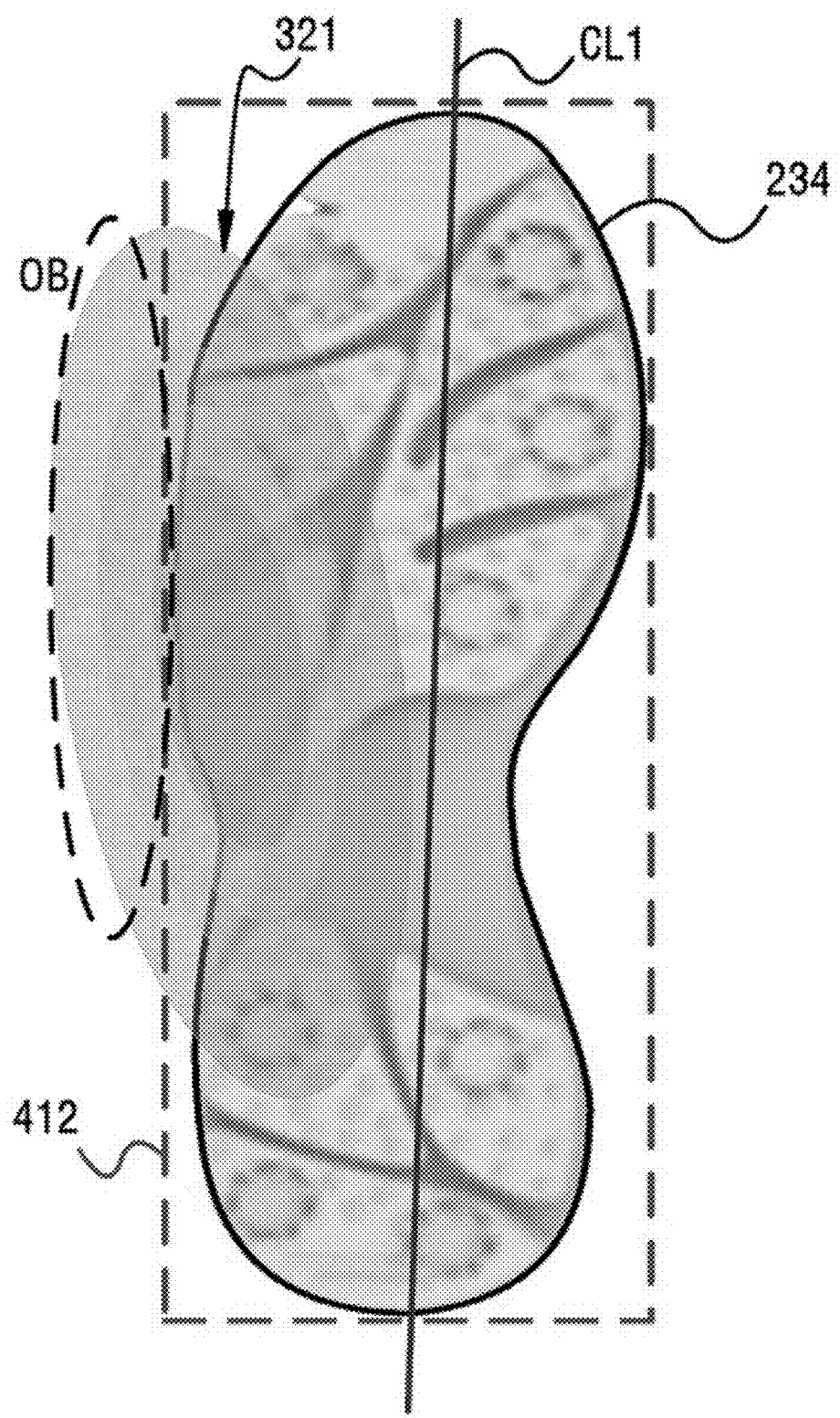

[Fig. 12]
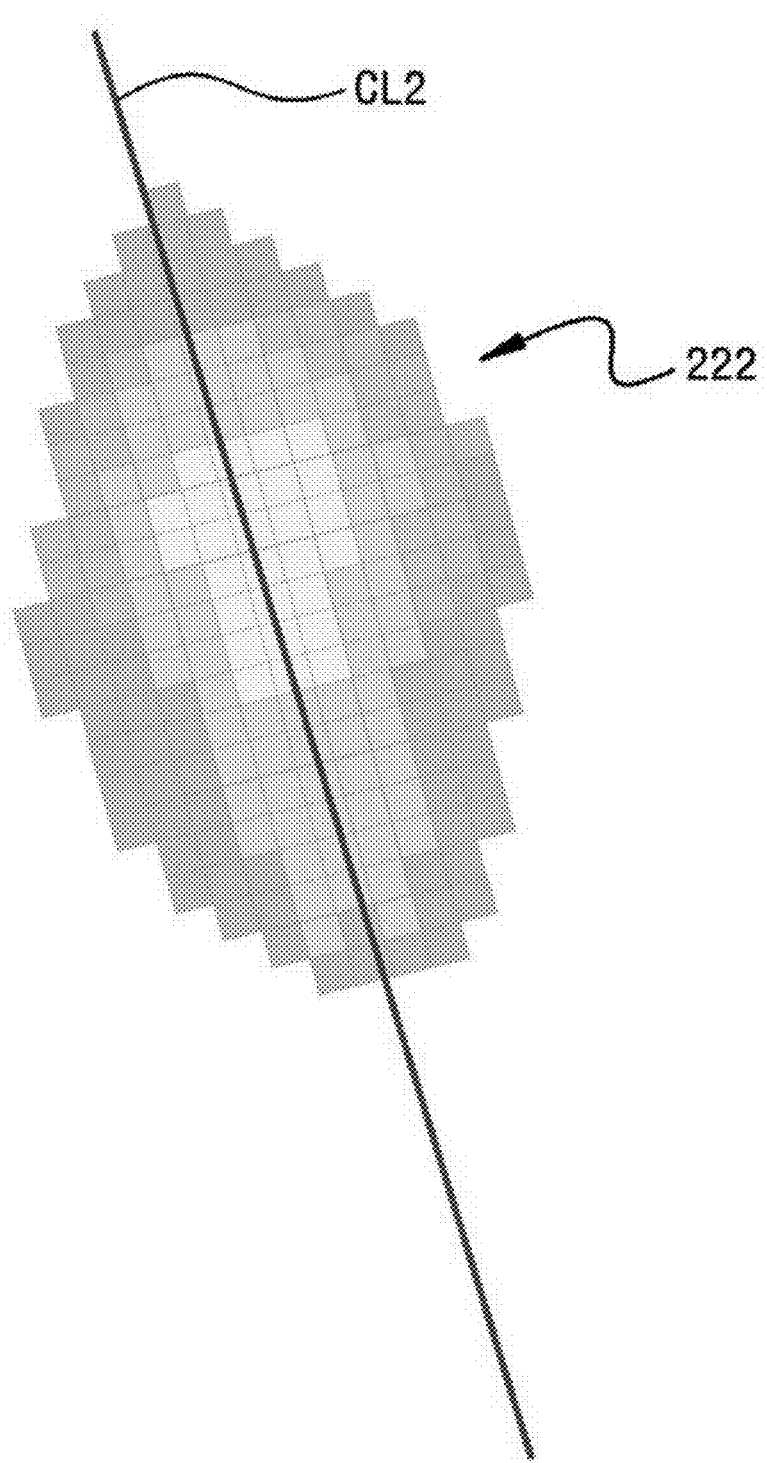

[Fig. 13]
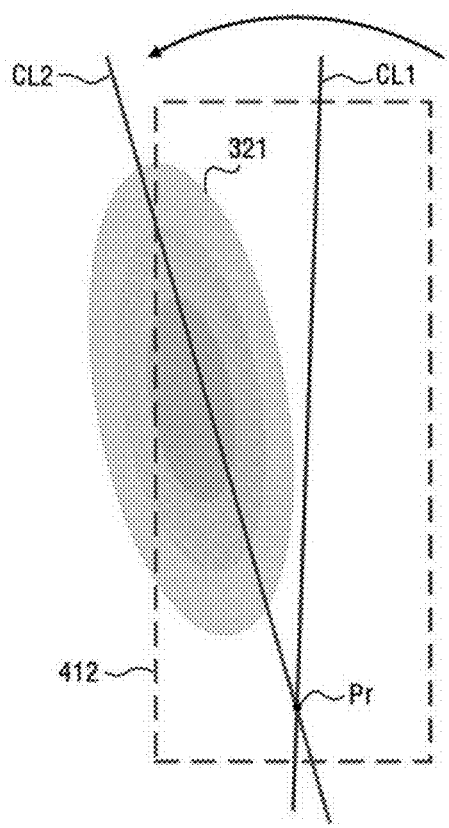
(a)
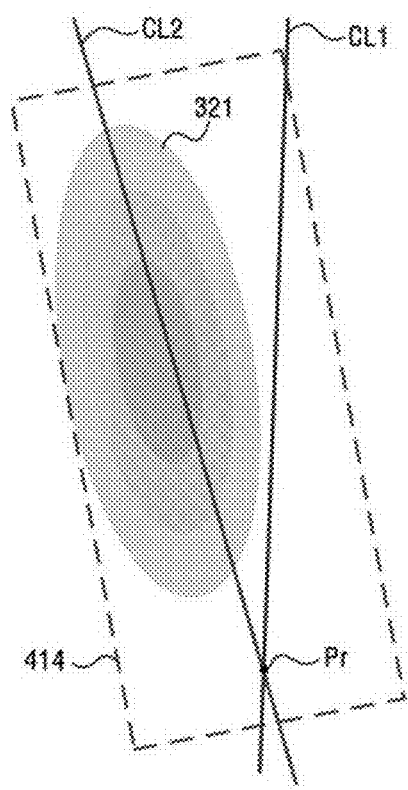
(b)

【Fig. 14】
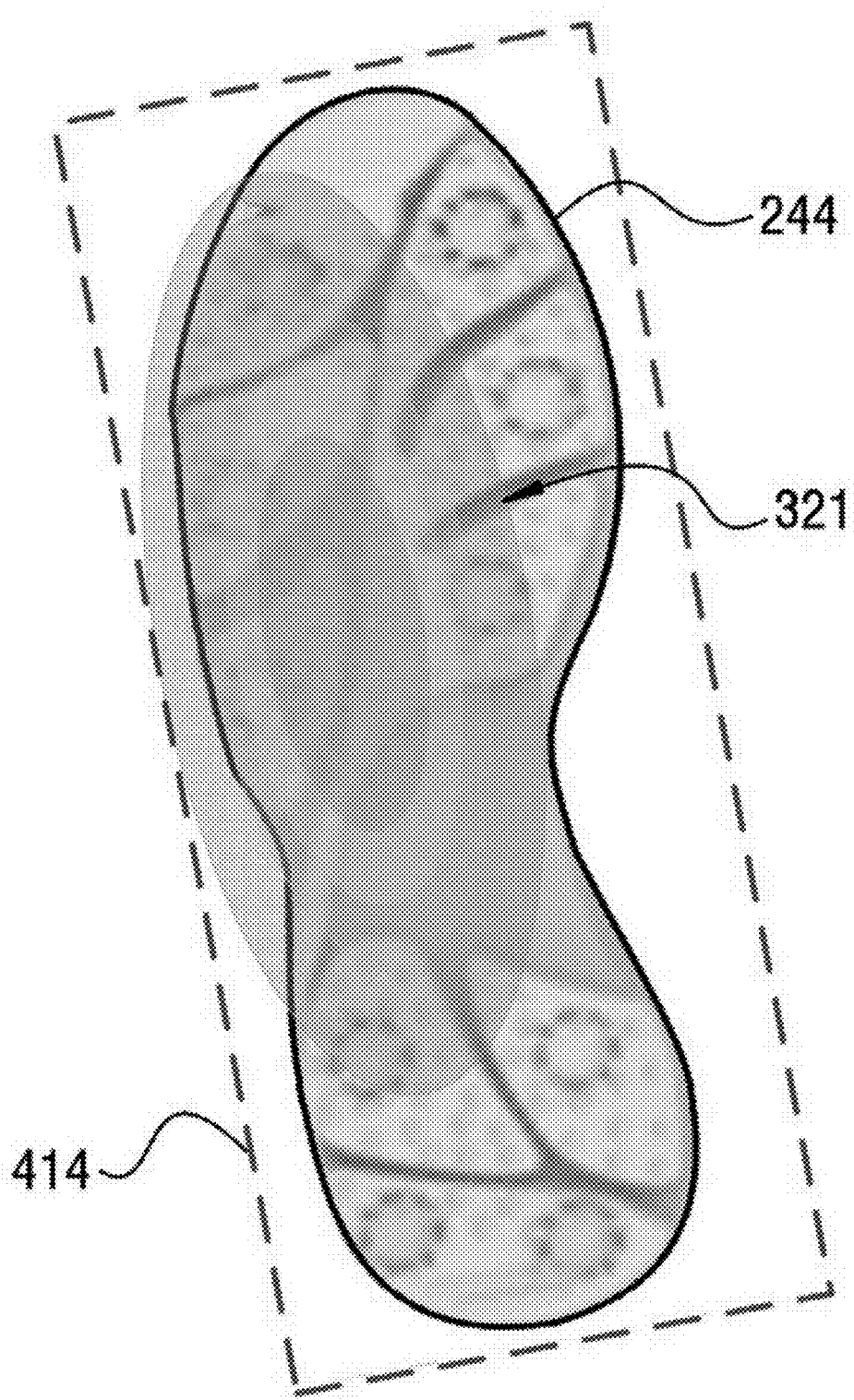

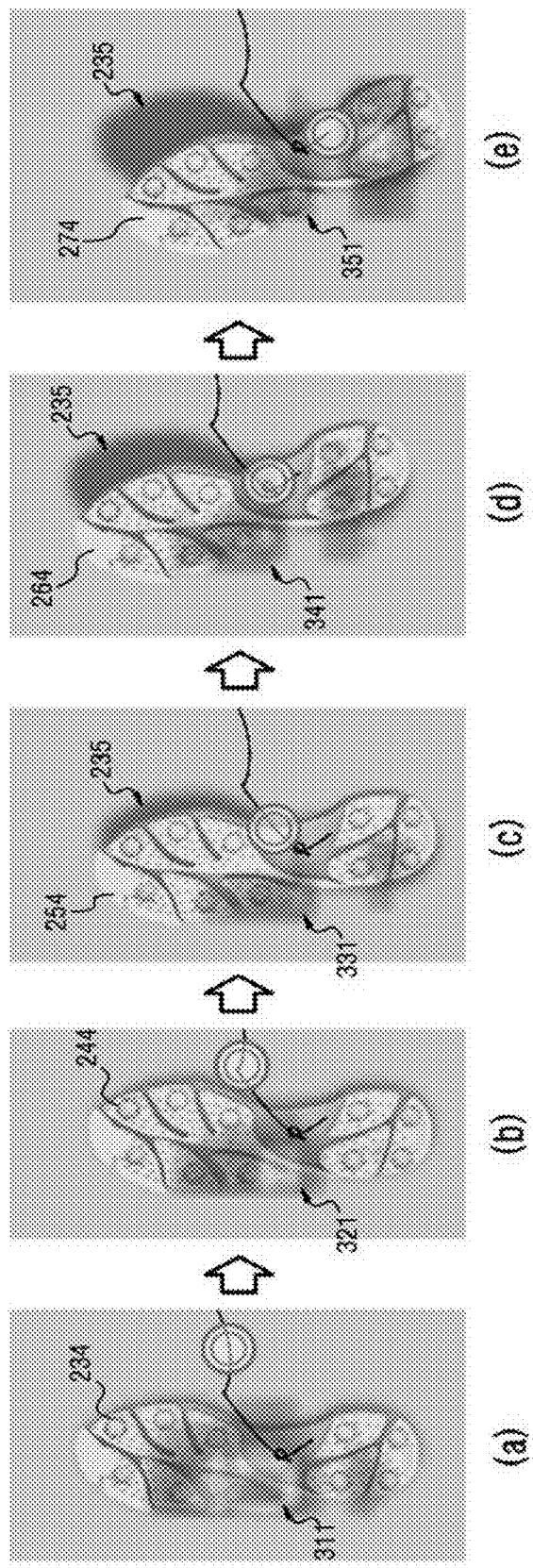
[Fig. 15]

[Fig. 16]
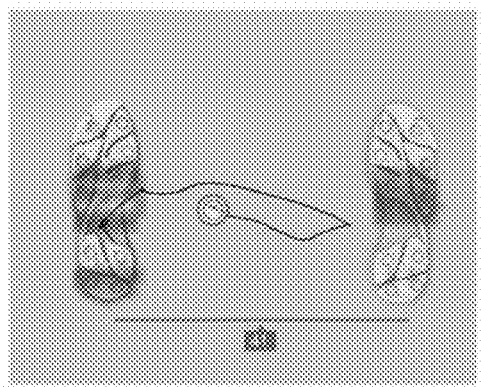
(a)
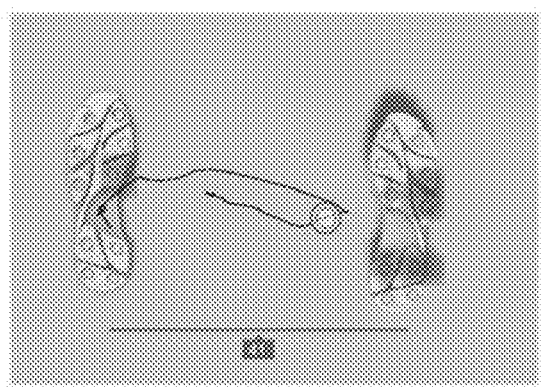
(b)
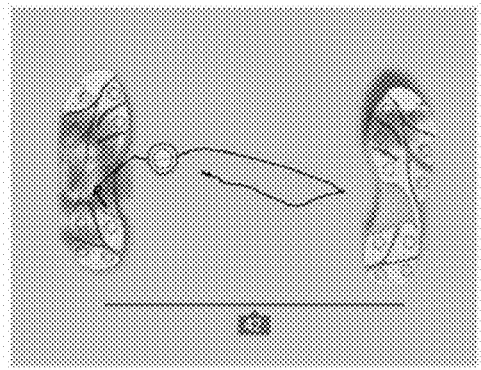
(c)
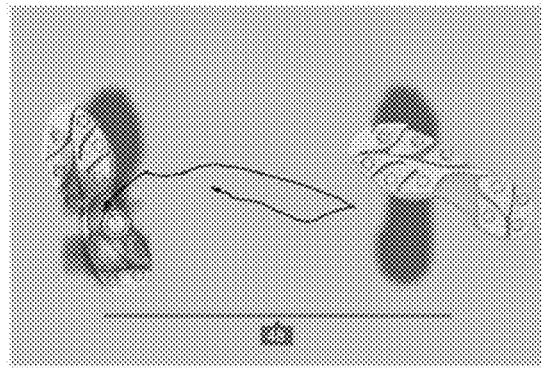
(d)

DEVICE FOR ANALYZING ATHLETIC POSTURE AND METHOD FOR GENERATING ANALYZING INFORMATION FOR ATHLETIC POSTURE

CROSS REFERENCE TO PRIOR APPLICATIONS

This application is a National Stage Application of PCT International Patent Application No. PCT/KR2015/008456 filed on Aug. 12, 2015, under 35 U.S.C. § 371, which claims priority to Korean Patent Application No. 10-2014-0104222 filed on Aug. 12, 2014, which are all hereby incorporated by reference in their entirety.

TECHNICAL FIELD

The present invention relates to an athletic posture analysis device and a method of generating athletic posture analysis information, and more particularly to an athletic posture analysis device and a method of generating athletic posture analysis information that are capable of analyzing an athletic posture, e.g. a golf swing posture, generating appropriate information regarding the athletic posture, and providing the generated information to a user.

BACKGROUND ART

With the great growth of sensor-related technology and sensing data analysis technology in recent years, there have been developed various kinds of analysis devices that are capable of sensing and analyzing an athletic posture of a user using updated sensing technology and analysis technology based thereon to accurately and precisely diagnose problems with the athletic posture of the user, to generate useful information necessary to correct the athletic posture of the user, and to provide the same to the user.

In particular, for golf, among various kinds of sports, it is very difficult to accurately assume a golf swing posture. In addition, problems tend to persist despite extensive practice. For these reasons, people correct their golf swing posture while constantly taking lessons from golf experts. In this way, golf swing practice is performed.

However, correcting the golf swing posture while constantly taking lessons from golf experts is limited in terms of cost and place (practice and lessons are only possible at golf driving ranges). Consequently, various kinds of golf swing posture analysis devices are under development, since the golf swing posture analysis devices are advantageous in terms of cost and place.

In particular, there has been frequently used an analysis device that analyzes the change in load applied to each of the feet of a golfer when the golfer takes a golf swing and provides information regarding analysis of the change in weight shift of the user. Examples of the analysis device that analyzes the change in weight shift of a golfer when the golfer takes a golf swing and provides analysis information are disclosed in Korean Registered Patent No. 10-0393352 and Japanese Patent Application Publication No. 1995-231968.

FIG. 1 is a view showing an example of information regarding analysis of the change in weight shift of a user according to a user's golf swing, generated by a conventional athletic posture analysis device.

Marks shown in the left part and the right part of FIG. 1 indicate the distribution of pressure applied to the feet of the user by the weight of the user when the user takes a swing in the state of standing on a foot plate provided with a pressure sensor.

Most information regarding analysis of the change in weight shift of the user provided by golf swing posture analysis devices that are disclosed as the conventional art or sold as products is provided as shown in FIG. 1.

The information regarding the distribution of pressure applied to the feet of the user by the weight of the user, as shown in FIG. 1, indicates how the load is applied to the left foot and the right foot of the user and how the load is changed in accordance with a user's swing. The above information is provided to the user. In FIG. 1, PD1 indicates the distribution of pressure applied to the left foot of the user by the weight of the user, and PD2 indicates the distribution of pressure applied to the right foot of the user by the weight of the user.

As can be seen from the information regarding the analysis of the change in weight shift of the user, however, it is difficult for the user to know the regions of the left foot and the right foot to which the weight of the user is applied, how much weight of the user is applied thereto, and how pressure is distributed, before a golf expert provides an explanation to the user. Consequently, the conventional athletic posture analysis device, which provides the above-mentioned analysis information, is used merely as a means for assisting golf experts in providing lesson information, and has limitations in use as a personal athletic posture analysis device or an athletic posture analysis device for home use.

Furthermore, the analysis information shown in FIG. 1 is difficult for the user to easily recognize. As a result, it is difficult for the user to reliably accept the analysis information. In addition, it is difficult for the user to recognize problems with the athletic posture of the user and to find solutions thereto. That is, it is difficult for the user to confidently recognize problems with the athletic posture of the user and find solutions thereto.

DISCLOSURE

Technical Problem

The present invention provides an athletic posture analysis device and a method of generating athletic posture analysis information that are capable of imaging the shape of each of the feet of a user based on the pressure applied to each of the feet of the user and displaying the distribution of pressure applied to each of the feet of the user in the case in which analysis of the change in weight shift of the user according to an athletic posture, e.g. a golf swing posture, is needed, and that are capable of tracking the changed distribution of pressure applied to each of the feet of the user to accurately display the foot image and the distribution of pressure applied to each of the feet of the user, even when the distribution of pressure applied to each of the feet of the user is changed according to the user's action, thereby very intuitively and visibly displaying athletic posture analysis information.

Technical Solution

In accordance with an aspect of the present invention, the above and other objects can be accomplished by the provision of an athletic posture analysis device for analyzing an athletic posture taken by a user who stands on a foot plate, the athletic posture analysis device including a pressure sensor plate provided at the foot plate for measuring the distribution of pressure applied to each of the feet of the user, who performs an athletic action, by the weight of the user, a display device for displaying athletic posture analysis information of the user, and a controller for performing control so as to display a predetermined foot image and information regarding the distribution of pressure applied to each of the feet of the user in an overlapping fashion through the display device and to track the position of each of the feet of the user changed according to the user's athletic action and display the foot image.

In accordance with another aspect of the present invention, there is provided a method of analyzing an athletic posture taken by a user who stands on a foot plate to generate athletic posture analysis information, the method including specifying the size and position of each of the feet of the user using information regarding the distribution of pressure applied to each of the feet of the user by the weight of the user, measured by a pressure sensor plate provided at the foot plate for measuring the distribution of pressure applied to each of the feet of the user, who performs an athletic action, by the weight of the user and mapping a predetermined foot image, displaying the mapped foot image and the information regarding the distribution of pressure applied to each of the feet of the user, measured by the pressure sensor plate, in an overlapping fashion, and tracking the position of each of the feet of the user changed according to the user's athletic action and displaying the foot image so as to correspond to the tracked position of each of the feet of the user.

Advantageous Effects

The athletic posture analysis device and the method of generating athletic posture analysis information according to the present invention are capable of imaging the shape of each of the feet of a user based on the pressure applied to each of the feet of the user and displaying the distribution of pressure applied to each of the feet of the user in the case in which analysis of the change in weight shift of the user according to an athletic posture, e.g. a golf swing posture, is needed. In addition, the athletic posture analysis device and the method of generating athletic posture analysis information according to the present invention are capable of tracking the changed distribution of pressure applied to each of the feet of the user to accurately display the foot image and the distribution of pressure applied to each of the feet of the user, even when the distribution of pressure applied to each of the feet of the user is changed according to the user's action, thereby very intuitively and visibly displaying athletic posture analysis information, thus enabling the user to easily recognize problems with the athletic posture of the user and to easily find the solution thereto.

Figure 1:
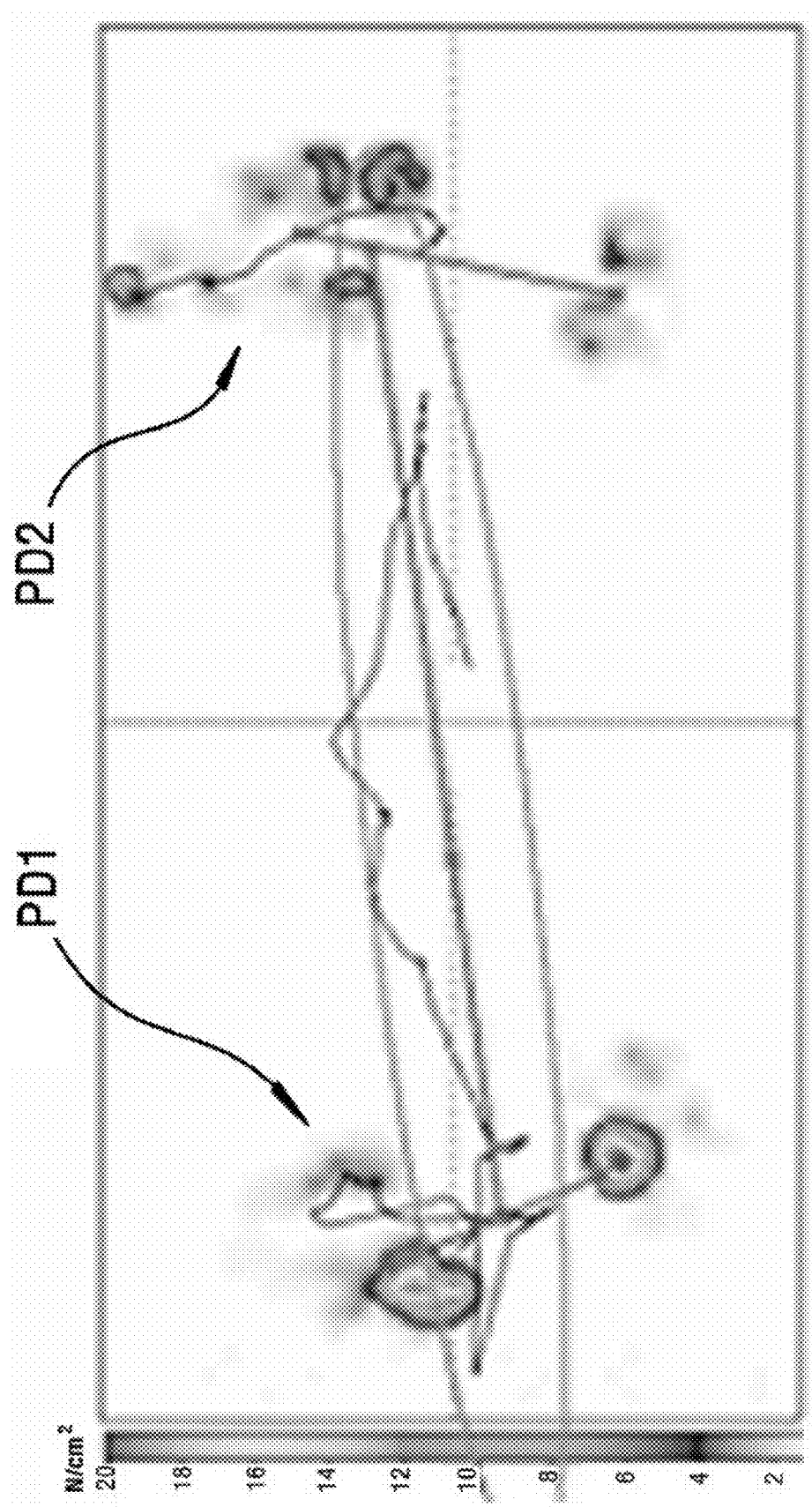
FIG. 1 is a view showing an example of user's athletic posture analysis information that is provided by a conventional athletic posture analysis device.
Figure 2:
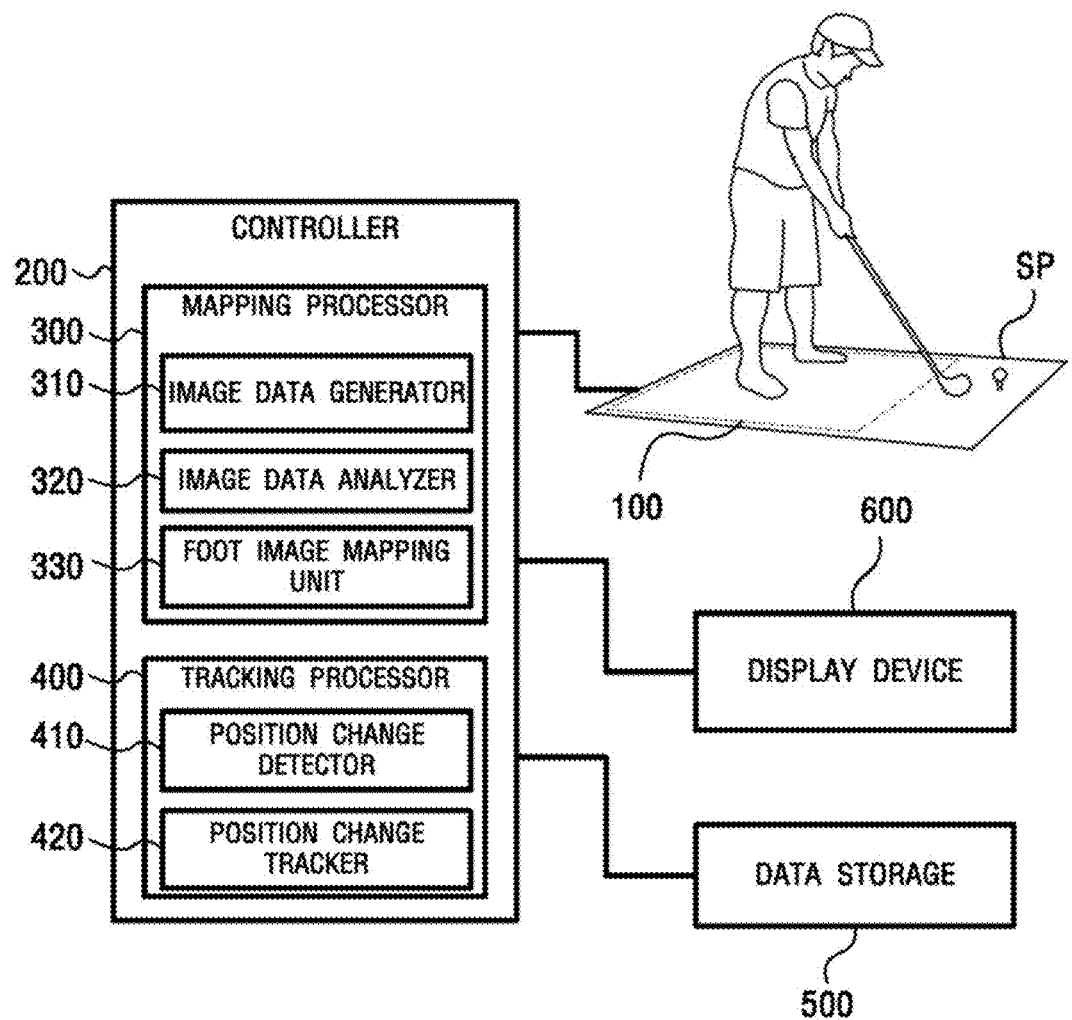
FIG. 2 is a block diagram showing the construction of an athletic posture analysis device according to an embodiment of the present invention.

(a) of FIG. 3 is a view showing an embodiment example of a foot plate, on which a user stands to take an athletic posture as shown in FIG. 2, and (b) of FIG. 3 is a view showing an embodiment example of a pressure sensor plate provided under a cover of the foot plate;

FIGS. 4 and 5 are flowcharts showing a method of generating athletic posture analysis information according to an embodiment of the present invention;

FIGS. 6 to 8 are views illustrating a concrete example of a foot image mapping process, which is performed in the method of generating athletic posture analysis information according to the embodiment of the present invention shown in FIG. 4;

(a) of FIG. 9 is a view showing only information regarding the distribution of pressure applied to each of the feet of the user without mapping the foot image, and (b) of FIG. 9 is a view showing the case in which the foot image mapped by the foot image mapping unit and the information regarding the distribution of pressure applied to each of the feet of the user are displayed in an overlapping fashion;

FIGS. 10 to 14 are views illustrating a concrete example of a foot position change tracking process, which is performed in the method of generating athletic posture analysis information according to the embodiment of the present invention shown in FIG. 5;

FIG. 15 is a view sequentially showing the distribution of pressure applied to each foot and the change of foot position after a golf ball is hit by the head of a golf club when the user takes a golf swing, acquired by the method of generating athletic posture analysis information shown in FIGS. 4 and 5; and FIG. 16 is a view showing an example of information regarding the change in weight shift of the user, which is analyzed and displayed by the athletic posture analysis device according to the embodiment of the present invention.

BEST MODE

Exemplary embodiments of an athletic posture analysis device and a method of generating athletic posture analysis information according to the present invention will be described in detail with reference to the accompanying drawings.

First, the construction of an athletic posture analysis device according to an embodiment of the present invention will be described with reference to FIG. 2.

The athletic posture analysis device according to the embodiment of the present invention is configured to analyze the change in weight shift of a user according to the athletic posture of the user and to provide information regarding such analysis. In particular, the athletic posture analysis device according to the embodiment of the present invention is useful for providing information regarding analysis of the change in weight shift of a user in a golf swing. The athletic posture analysis device according to the embodiment of the present invention is applicable to the analysis of various athletic postures that require analysis of the change in weight shift of a user, besides golf.

Hereinafter, a description will be given of the provision of information regarding the change in weight shift of a user in a golf swing using the athletic posture analysis device according to the embodiment of the present invention and a method of generating athletic posture analysis information according to an embodiment of the present invention.

As shown in FIG. 2, the athletic posture analysis device according to the embodiment of the present invention may include a pressure sensor plate 100, a controller 200, a data storage 300, and a display device 400.

The pressure sensor plate 100 is a device that is provided at a foot plate SP, on which a user stands to take an athletic posture, e.g. a golf swing posture, to measure the distribution of pressure applied to the feet of a user by the weight of the user.

In the conventional art, a load cell is usually used to measure the weight shift of a user. In the athletic posture analysis device according to the embodiment of the present invention, the pressure sensor plate 100 includes a plurality of pressure sensors arranged in a matrix fashion, as shown in (a) and (b) of FIG. 3. Preferably, therefore, it is possible for each of the pressure sensors to accurately measure the pressure applied to the feet of the user by the weight of the user.

(a) of FIG. 3 is a view showing an embodiment example of the foot plate SP, on which the user stands to take an athletic posture as shown in FIG. 2, and (b) of FIG. 3 is a view showing an embodiment example of the pressure sensor plate 100, which is provided under a cover 101 of the foot plate SP.

As shown in (b) of FIG. 3, the pressure sensor plate 100 may include a plurality of pressure sensors 110, such as force sensing resistors (FSRs). The FSRs may be arranged in a matrix fashion to constitute the pressure sensor plate 100.

Each of the pressure sensors 110 of the pressure sensor plate 100 measures the pressure applied to each of the feet of the user depending on the athletic posture of the user, and transmits measurement information to the controller 200.

The controller 200 performs control so as to generate information regarding the distribution of pressure applied to the feet of the user by the weight of the user using the measurement information, received from the pressure sensor plate 100, and to display the generated information through the display device 400.

The athletic posture analysis device according to the embodiment of the present invention is configured to very intuitively and visibly display information regarding the distribution of pressure applied to the feet of the user by the weight of the user, measured by the pressure sensor plate 100, through the display device. To this end, the controller 200 performs control so as to specify the size and position of each of the feet of the user using the measurement information, received from the pressure sensor plate, to map a predetermined foot image, and to display the mapped foot image and information regarding the distribution of pressure applied to the feet of the user in an overlapping fashion.

In addition, when the distribution of pressure applied to each of the feet of the user is changed according to the user's action, the position of each of the feet is tracked, and the mapped foot image and information regarding the distribution of pressure applied to each of the feet of the user are displayed in an overlapping fashion while the mapped foot image is displayed at the position of each of the feet tracked according to the changed distribution of pressure applied to each of the feet of the user.

In order to perform the above function, as shown in FIG. 2, the controller 200 may include a mapping processor 300 and a tracking processor 400.

The mapping processor 300 performs a function of specifying the size and position of each of the feet of the user using data indicating the pressure applied to each of the feet of the user based on the information measured by the pressure sensor plate 100 and mapping a predetermined foot image. Specifically, the mapping processor 300 may include an image data generator 310, an image data analyzer 3220, and a foot image mapping unit 330.

The image data generator 310 performs a function of generating data of an image configured to be easy to analyze, e.g. a grayscale image, indicating the distribution of pressure applied to each of the feet of the user, measured by the pressure sensor plate 100.

The image data analyzer 320 performs a function of analyzing the image data, generated by the image data generator 310, to specify information regarding the size and position of each of the feet of the user standing on the pressure sensor plate 100.

The foot image mapping unit 330 performs a function of mapping a predetermined foot image, stored in the data storage 500 (which may store various kinds of images, such as an image indicating the sole of each shoe and an image indicating the sole of each of the feet, in advance), so as to coincide with the size and position of each of the feet of the user, specified by the image data analyzer 320.

The functions of the image data generator 210, the image data analyzer 220, and the foot image mapping unit 230 will be described below in more detail.

Meanwhile, the tracking processor 400 performs a function of tracking the position of each of the feet when the distribution of pressure applied to each of the feet of the user is changed according to the user's action and displaying the foot image at the tracked position of each of the feet. Specifically, as shown in FIG. 2, the tracking processor 400 may include a position change detector 410 and a position change tracker 420.

The position change detector 410 performs a function of setting a reference region so as to include the foot image mapped by the foot image mapping unit 330 and detecting the portion of each of the feet of the user at which the distribution of pressure applied to each of the feet of the user deviates from the reference region when the distribution of pressure applied to each of the feet of the user is changed according to the user's action.

The position change tracker 420 performs a function of calculating a center of rotation using data indicating the changed distribution of pressure applied to each of the feet of the user, rotating the reference region about the center of rotation until the data indicating the changed distribution of pressure applied to each of the feet of the user are included in the reference region, and displaying the foot image so as to correspond to the rotated reference region.

The position change detector 410 and the position change tracker 420 will be described in more detail below.

Meanwhile, the data storage 300, shown in FIG. 2, is a component for storing data that are necessary for the controller 200 to perform control so as to perform information analysis, mapping, and tracking and for the display device 600 to display athletic posture analysis information.

The display device 600 is a component for displaying athletic posture analysis information under the control of the controller 200.

Hereinafter, a method of generating athletic posture analysis information, performed by the athletic posture analysis device according to the embodiment of the present invention, will be described with reference to FIGS. 4 and 5, using the components of the block diagram shown in FIG. 2. FIG. 4 is a flowchart showing a foot image mapping process, which is performed in a method of generating athletic posture analysis information according to an embodiment of the present invention, and FIG. 5 is a flowchart showing a foot position change tracking process, which is performed in the method of generating athletic posture analysis information.

First, the foot image mapping process, which is performed by the mapping processor 300 of the controller 200, will be described with reference to FIG. 4.

When a user takes a golf swing posture on the foot plate provided with the pressure sensor plate shown in FIG. 3 in order to take a golf swing, each of the pressure sensors of the pressure sensor plate measures the pressure applied to each of the feet of the user by the weight of the user and transmits measurement information to the controller, whereby the controller acquires information regarding the distribution of pressure applied to each of the feet of the user (S10).

The image data generator of the controller generates image data indicating the distribution of pressure applied to each of the feet of the user using the acquired information regarding the distribution of pressure applied to each of the feet of the user (S20).

The image data analyzer of the controller performs control so as to extract a center line from an image data set, generated at step S20 (S30). It is preferable to extract the longest major axis passing through the image data set as the center line. A detailed example thereof will be described below.

Meanwhile, the image data analyzer of the controller performs control so as to distinguish between the front part and the rear part of each of the feet using opposite ends of the image data set through which the center line passes, extracted at step S30, i.e. using the portions of the center line that intersect the contour of the image data set (S40). The front part and the rear part of each of the feet may be distinguished using shape characteristics of the image data set, or may be distinguished based on data distribution.

Meanwhile, the image data analyzer of the controller performs control so as to set a check box at the contour of the image data set on the basis of the center line (S50) and to analyze the center line, the check box, and the data distribution of the image data set to specify the size and position of each of the feet (S60).

When the size and position of each of the feet are specified from the image data set, indicating the information regarding the distribution of pressure applied to each of the feet of the user, as described above, the foot image mapping unit of the controller performs control so as to determine the size of a predetermined foot image based on information regarding the specified size of each of the feet, to map the foot image having the determined size so as to coincide with information regarding the specified position of each of the feet, and to display a foot image having a size and a position corresponding to the image data set (S70).

The controller performs control so as to display the mapped foot image and the information regarding the distribution of pressure applied to each of the feet of the user, acquired by the pressure sensor plate, in an overlapping fashion (S80). As a result, it is possible for the user to very intuitively recognize the change in weight shift of the user according to the golf swing posture of the user.

Next, the foot position change tracking process, which is performed by the tracking processor 400 of the controller 200, will be described with reference to FIG. 5.

As shown in FIG. 4, the size of each of the feet of the user is specified using the pressure applied to each of the feet of the user by the weight of the user when the user takes the athletic posture in the state of standing on the pressure sensor plate and the foot image corresponding thereto is specified. The foot position change tracking process is a process of sensing and tracking the change in position of each of the feet of the user according to the user's action, adjusting the position of the specified foot image based on the tracking results, and displaying the foot image the position of which has been adjusted.

The position change detector of the controller sets a reference region so as to include the foot image mapped according to the foot image mapping process shown in FIG. 4 (S100). The reference region may be set as a quadrangular region that is circumscribed about the mapped foot image, or may be set as a quadrangular region that is spaced apart from the contour of the mapped foot image by a predetermined offset. In addition, the reference region may be defined to have an oval shape, as an alternative to the quadrangular shape, or may be defined to have a shape that is identical to the shape of the foot image but is spaced apart from the contour of the foot image by a predetermined distance.

The position change detector of the controller detects the portion of each of the feet of the user at which the distribution of pressure applied to each of the feet of the user deviates from the reference region based on the distribution of pressure applied to each of the feet of the user received from the pressure sensor plate according to the user's action (S110).

If a portion of each of the feet of the user at which the distribution of pressure applied to the corresponding foot of the user deviates from the reference region according to the user's action is present, the position change tracker of the controller calculates a center of rotation using data indicating the changed distribution of pressure applied to each of the feet of the user (S120), and rotates the reference region about the center of rotation until the data indicating the changed distribution of pressure applied to each of the feet of the user are included in the reference region (S130).

The position change tracker of the controller stops the rotation of the reference region when the data indicating the changed distribution of pressure applied to each of the feet of the user are included in the reference region while the reference region is rotated about the center of rotation, and displays the foot image so as to correspond to the rotated reference region (S140). In this way, the change in position of each of the feet of the user is tracked.

Hereinafter, the respective steps of the foot image mapping process shown in the flowchart of FIG. 4 will be described in detail with reference to FIGS. 6 to 8.

(a) of FIG. 6 is a view showing an example of a grayscale image, including pixels having brightness values indicating the distribution of pressure applied to each of the feet of the user by the weight of the user, generated by the image data generator of the controller of the athletic posture analysis device according to the embodiment of the present invention, and (b) of FIG. 6 is a view showing an example of a foot image that is mapped by the foot image mapping unit of the controller in accordance with the analysis of image data regarding the distribution of pressure applied to each of the feet of the user.

The image data generator of the controller of the athletic posture analysis device according to the embodiment of the present invention receives values measured by the pressure sensors 110 (see FIG. 3) in the state in which the user stands on the pressure sensor plate 100 (see FIG. 3), and generates data of a grayscale image having pixel values (i.e. brightness values) corresponding to the values measured by the pressure sensors, as shown in (a) of FIG. 6. The brighter portions of an image data set 212 shown in (a) of FIG. 6 are the portions of each of the feet to which higher pressure is applied.

A foot image 232 shown in (b) of FIG. 6 is a predetermined image, and an image indicating the sole of a golf shoe is shown in (b) of FIG. 6. However, various foot images may be set. For example, an image indicating the sole of a bare foot or an image indicating a general sports shoe may also be set.

However, only the design of the foot image 232 shown in (b) of FIG. 6 is set in advance, but the size and position of each of the feet are not set. For this reason, the size and position of each of the feet are specified through analysis of the image data set 212 shown in (a) of FIG. 6, the size and position of the foot image 232 are adjusted so as to coincide with the specified size and position of each of the feet, and the foot image 232 is mapped.

In the method of specifying the size of each of the feet using the data of the grayscale image, the contour of the image data set may be extracted, the extracted contour may be regarded as the shape of each of the feet, and the width of each of the feet (i.e. the largest length of each of the feet in the lateral direction) may be calculated, whereby the size of each of the feet may be specified.

In addition, the center line of the image data set may be extracted, and the size and position of each of the feet may be specified based on specific criteria, which will be described in detail hereinafter.

In order to specific the size and position of each of the feet using the image data shown in (a) of FIG. 6, it is necessary to extract a center line CL of the image data set 212 and to distinguish between the front part and the rear part of each of the feet from the image date set 212.

As shown in (a) of FIG. 6, the image data analyzer extracts the longest major axis passing through the image data set 212 as the center line CL.

The center line CL may be extracted using a line fitting algorithm, such as a method of least squares or a random sample consensus (RANSAC) algorithm. In consideration of data distribution, the RANSAC algorithm is more preferably used to extract the center line. The RANSAC algorithm is a well-known line fitting algorithm, and therefore a detailed description thereof will be omitted.

The center line CL extracted as described above is a basis for mapping the foot image.

Meanwhile, in the case in which the longest major axis passing through the image data set is extracted as the center line CL, as described above, the center line inevitably passes through the front part and the rear part of each of the feet.

Consequently, in the case in which the center line CL is extracted, as described above, opposite ends of the image data set through which the center line CL passes may correspond to the front part and the rear part of each of the feet, and the front part and the rear part of each of the feet may be distinguished based on the entire shape of a portion of the image data set 212 adjacent to point P1 and the entire shape of a portion of the image data set 212 adjacent to point P2.

That is, since the portion of the image data set having a gentle slope corresponds to the rear part of each of the feet, the image data analyzer of the present invention may analyze the shape characteristics of the image data set at the opposite ends of the image data set on the basis of the center line CL to distinguish between the front part and the rear part of each of the feet.

However, information regarding the distribution of pressure applied to each of the feet of the user may not be perfect depending on the kind of the shoes that the user who stands on the pressure sensor plate 100 (see FIG. 3) wears or the state in which each of the feet of the user pushes the pressure sensor plate. In this case, it may be difficult to distinguish between the front part and the rear part of each of the feet based on the shape characteristics of the image data set.

In an example, in the case in which hobnails or spikes are present in the sole of the shoe, the pressure applied to each of the feet may not be completely transmitted to the pressure sensors. In another example, in the case in which the user takes an athletic posture while lifting toes, the front part of each of the feet may not be completely transmitted to the pressure sensors. As a result, some of the image data may not be completely displayed.

Consequently, the image data analyzer of the present invention may distinguish between the front part and the rear part of each of the feet from the image data set using another method of distinguishing between the front part and the rear part of each of the feet together with the method of distinguishing between the front part and the rear part of each of the feet based on the shape characteristics of the image data set or separately from the method of distinguishing between the front part and the rear part of each of the feet based on the shape characteristics of the image data set.

To this end, the image data analyzer may set a check box 214 at the contour of the image data set 212 on the basis of the center line CL, and may specify the size of each of the feet using the check box.

That is, as shown in (a) of FIG. 6, the image data analyzer may generate a first vertical line L1 that abuts on the right side of the image data set 212 on the basis of the center line CL and that is parallel to the center line CL, a second vertical line L2 that abuts on the left side of the image data set 212 on the basis of the center line CL and that is parallel to the center line CL, a first horizontal line L3 that abuts on the front side of the image data set 212 and that is perpendicular to the center line CL, and a second horizontal line L4 that abuts on the rear side of the image data set 212 and that is perpendicular to the center line CL in order to set a check box 214 that is defined by the first vertical line L1, the second vertical line L2, the first horizontal line L3, and the second horizontal line L4.

As shown in (a) of FIG. 6, regions having very small data values (i.e. brightness values or measured pressure values) or no data values exist in the check box 214, in which the image data set 212 is located. For example, the pressure value measured in an inner concave region of each of the feet (a region denoted by Rv in (b) of FIG. 6), which is formed based on the structural characteristics of the sole of each of the feet, is small or null. When an image of each of the feet is generated, therefore, the brightness value of the image corresponding to the region of each of the feet is very small or null. The above-mentioned region will be referred to as an "empty region."

One or more empty regions may exist in the image data set indicating the distribution of pressure applied to each of the feet depending on the state of each of the shoes or the posture of each of the feet. In consideration of the structure of each of the feet, the inner concave region of each of the feet is displayed as the largest empty region. In the case in which one or more empty regions are detected in the image data set, therefore, the largest empty region may be determined to be the inner concave region of each of the feet, and the front part and the rear part of each of the feet may be distinguished based thereon. The largest empty region is denoted by Re in the figure.

The image data analyzer of the present invention may detect the empty region Re, and may determine the part of the image data set 212 in which the detected empty region Re is located, or may determine the side of the image data set 212 to which the detected empty region Re is closer on the basis of the center line CL to distinguish between the front part and the rear part of each of the feet.

Meanwhile, as described above, the check box 214 may be set on the basis of the center line CL, and the width W of the set check box 214 may be calculated to specify the size of each of the feet. Then, the width X of the foot image 232 shown in (b) of FIG. 6 may be adjusted to coincide with the width W of the check box 214, whereby it is possible to obtain a foot image having a specified size of each of the feet from the image data.

That is, since, when the width X of the foot image is reduced or magnified so as to coincide with the width W of the set check box, the length Y of the foot image is reduced or magnified accordingly (i.e. since the ratio of X to Y is fixed, the size of the foot image is adjusted when X is adjusted so as to coincide with W), information regarding the width X of the foot image may be specified using the check box 214 of the image data set 212, whereby the size of each of the feet may be specified.

The size of each of the feet may be specified on the basis of the length of the image data set 212 shown in (a) of FIG. 6, i.e. the length D of the check box 214. Since the front part of each of the feet may not be completely displayed as the image data depending on the state of the shoe of the user or the posture of each of the feet of the user, as described above, however, the length D of the check box 214 may not reflect the correct value. For this reason, there may be limitations in determining the correct size of each of the feet on the basis of the length D of the check box 214.

Hereinafter, the operation of detecting the heel region of each of the feet in order to specify the position of each of the feet from the image data set 212 will be described.

As described above, the distribution of pressure applied to each of the feet of the user may not be completely displayed depending on the state of the shoe of the user or the posture of each of the feet of the user. Even in this case, the data of the image data set corresponding to the rear part of each of the feet are completely displayed, since most of the weight of the body of the human being is applied to the heel of each of the feet due to the structural characteristics of the body (unless the heel of each of the feet is not lifted in the athletic posture).

Consequently, it is preferable to detect the heel region of each of the feet from the image data set and to specify the position of each of the feet based on the detected heel region of each of the feet.

FIG. 7 is a view illustrating an example of a method of specifying the heel region of each of the feet from the image data set 212.

As shown in FIG. 8, the sum of data values of data arranged from the start point P2 of the rear part of each of the feet in the direction indicated by an arrow a and in the direction indicated by an arrow b is calculated.

The calculated sum of the data values is shown as a graph having a pattern shown in FIG. 7.

The distribution of the sum of the data values from the start point P2 of the rear part of each of the feet forms a pattern that is abruptly increased, is abruptly decreased, and is then gradually increased, as shown in the graph of FIG. 7. The reason that the sum of the data values is abruptly decreased is because the data value of the data corresponding to the inner part of each of the feet is very small or null. In the case in which an appropriate value is set as a reference value n, as shown in FIG. 7, the region having the sum of the data values higher than the reference value may be specified as the heel region Rh of each of the feet.

The reference value n may be set as the value at the position at which the graph is started (i.e. the sum of the data values of the data from the start point P2 of the rear part of each of the feet in the direction indicated by the arrow b). The reference value n may also be set as a value having a predetermined offset value applied thereto (for example, a value obtained by adding a value preset as the offset value to the value at the start point P2 may be set as the reference value). In addition, the reference value n may be set as a predetermined value.

After the heel region of each of the feet is specified using the distribution of the sum of the data values, as described above, the image data analyzer of the present invention extracts a center point Pc of the heel region Rh of each of the feet based on the specified heel region of each of the feet, as shown in (a) of FIG. 8.

The heel region Rh of each of the feet specified from the image data set 212 may be a region set by data located outside the data within the range set based on the reference value n in the graph of FIG. 7, or may be a region that approximates a circle, as shown in FIG. 8.

The center point Pc may be set as the center of gravity of the specified heel region Rh of each of the feet, or may be set as a point that forms the spatial center of the specified heel region Rh of each of the feet.

Meanwhile, it is necessary to specify a heel region Fh of the foot image and a center point Fc of the heel region with respect to the foot image 232 shown in (b) of FIG. 8. This is information that is preset as the size of the foot image is determined. That is, the above information may be set when the size of the foot image is determined, since information regarding the foot image is predefined and predetermined information.

In response to the center line CL of the image data set 212, as shown in (b) of FIG. 9, the longest major axis passing through the foot image 232 is extracted as a center line FL, which is information that is preset as the size of the foot image is determined.

Consequently, the center line CL and the center point Pc of the heel region Rh of each of the feet are extracted from the image data, as described above, whereby information regarding the position of each of the feet may be specified. The foot image mapping unit of the present invention adjusts the center point Fc of the heel region Fh of the foot image 232, the size of which is determined, so as to correspond to the center point Pc of the heel region Rh of each of the feet extracted from the image data, and maps the foot image 232 in the state in which the center line FL of the foot image 232 corresponds to the center line CL extracted from the image data. That is, the foot image is displayed in the state of being adjusted so as to coincide with the size and position of each of the feet specified from the image data.

The controller of the athletic posture analysis device according to the embodiment of the present invention performs control such that the foot image mapped by the foot image mapping unit and the information regarding the distribution of pressure applied to each of the feet of the user, received from the pressure sensor plate, are displayed through the display device in an overlapping fashion.

FIG. 9 shows an example in which the mapped foot image and the information regarding the distribution of pressure applied to each of the feet of the user are displayed in an overlapping fashion, as described above.

(a) of FIG. 9 is a view showing only the information regarding the distribution of pressure applied to each of the feet of the user without mapping the foot image, and (b) of FIG. 9 is a view showing the case in which the foot image mapped by the foot image mapping unit and the information regarding the distribution of pressure applied to each of the feet of the user are displayed in an overlapping fashion.

The left part 311 of athletic posture analysis information 310 shown in (a) of FIG. 9 indicates information regarding the distribution of pressure applied to the left foot of the user by the weight of the user, measured by the pressure sensor plate, and the right part 312 of the athletic posture analysis information 310 indicates information regarding the distribution of pressure applied to the right foot of the user by the weight of the user, measured by the pressure sensor plate.

In addition, athletic posture analysis information 320 shown in (b) of FIG. 9 indicates that a foot image 234 corresponding to the left foot and a foot image 236 corresponding to the right foot are mapped and displayed in the state in which the information 311 regarding the distribution of pressure applied to the left foot of the user and the information 312 regarding the distribution of pressure applied to the right foot of the user are overlapped thereon.

The controller of the athletic posture analysis device according to the embodiment of the present invention may perform control such that the position of the mapped foot image is finely adjusted based on the information regarding the distribution of pressure applied to each of the feet of the user overlapped thereon, whereby athletic posture analysis information is finally displayed.

For example, upon determining that the information regarding the distribution of pressure applied to each of the feet of the user is very far from the mapped foot image or upon determining that the size of the foot image is much smaller or larger than the information regarding the distribution of pressure applied to each of the feet of the user, the controller may perform control such that the size or position of the mapped foot image is finely adjusted so as to correspond to the information regarding the distribution of pressure applied to each of the feet of the user.

In the process of mapping the predetermined foot image using the information regarding the distribution of pressure applied to each of the feet of the user when the user assumes an athletic posture in the state of standing on the pressure sensor plate, the foot image may be more accurately mapped as the image data indicating the distribution of pressure applied to each of the feet of the user are more accurately extracted. To this end, the controller may store the heights, weights, ages, body types, and foot sizes of various users, the kinds of shoes that the users wear, etc. in advance in the form of a database, and may correct the image data indicating the extracted distribution of pressure applied to each of the feet of the user using the database, whereby it is possible to generate more accurate data.

For example, in the case in which a golf swing posture is analyzed, information regarding the shape or size of image data indicating the distribution of pressure applied to each of the feet of users according to the heights, weights, body types, etc. of the users based on various kinds of golf shoes may be stored in advance in the form of a database, and image data indicating the distribution of pressure applied to each of the feet of a current user may be generated using the database.

In this case, of course, the athletic posture analysis device according to the embodiment of the present invention preferably includes a means for inputting and storing information regarding the height, weight, etc. of the user who stands on the pressure sensor plate.

In this case, however, an incorrect athletic posture of the user may be interpreted as a correct athletic posture of the user as the result of excessive correction. For this reason, only minor corrections must be performed using the information stored in the form of the database.

In addition, foot image data indicating the address postures of professional golfers may be stored in the form of a database with respect to respective golf shoes, the difference between the foot image data for one selected from among the professional golfers and the foot image data for a user similar in height, weight, and body type to the selected professional golfer may be analyzed, and the analysis results may be provided to the user.

Hereinafter, the respective steps of the foot position change tracking process shown in the flowchart of FIG. 5 will be described in detail with reference to FIGS. 10 to 14.

FIG. 10 is a view showing the state in which the foot image 234 is mapped according to the flowchart shown in FIG. 4 and the mapped foot image and information 311 regarding the distribution of pressure applied to each of the feet of user are displayed in an overlapping fashion. The shown information regarding the distribution of pressure applied to each of the feet of user is simply expressed in an oval shape for simplicity of the figure.

The position change detector of the controller of the present invention sets a reference region 412 based on the mapped foot image 234, as shown in FIG. 10.

The reference region 412 may be defined and set to have various shapes and sizes, as previously described. In the following description, the reference region 412 is defined as a quadrangular region that is circumscribed about the foot image 234. Of course, reference regions having different shapes and sizes may be defined and set. In this case, the same principle is applied.

The state of distribution of pressure applied to each of the feet of user is changed according to the user's action, e.g. the user's golf swing action. When the user performs the action without moving his/her feet, the information regarding the distribution of pressure applied to each of the feet of user by the weight of the user, received from the pressure sensor plate, is changed within the reference region 412. As a result, the foot image 234 is not changed, and only the information 311 regarding the distribution of pressure applied to each of the feet of user is changed.

However, when the user moves his/her feet while the user performs the action with the result that the feet of the user deviate from the original positions thereof, the information regarding the distribution of pressure applied to each of the feet of user by the weight of the user, received from the pressure sensor plate, deviates from the reference region 412.

Of course, sensitivity in position change tracking based on the change of the information regarding the distribution of pressure applied to each of the feet of user may be changed depending on the size of the reference region 412 that is set. That is, in the case in which the reference region is set to have a large size, the foot position change may be tracked only when the distribution of pressure applied to each of the feet of user is greatly changed to a predetermined level or more. On the other hand, in the case in which the reference region is set to have a small size, the foot position change may be tracked even when the distribution of pressure applied to each of the feet of user is slightly changed.

In the case in which information 321 regarding the distribution of pressure applied to each of the feet of user is changed according to the user's action and a portion OB of the pressure distribution information deviates from the reference region 412 (in this case, the portion of the pressure distribution information that deviates from the reference region may be set in advance), as shown in FIG. 11, the position change detector of the controller of the present invention may detect the portion OB of the pressure distribution information that deviates from the reference region 412, whereby the foot position change is tracked.

In order to track the foot position based on the changed pressure distribution information 321, the position change tracker of the controller of the present invention extracts the longest major axis passing through the mapped foot image 234 as a center line CL1 of the mapped foot image 234. The center line CL1 will be referred to as a first center line.

Image data of a grayscale image are generated in response to the changed pressure distribution information 321, which is shown in FIG. 12. The generation of image data of a grayscale image using the information regarding the distribution of pressure applied to each of the feet of user is performed in the same manner as the generation of image data indicating the distribution of pressure applied to each of the feet of user, performed by the image data generator of the controller in the foot image mapping process.

When an image data set 222 corresponding to the changed distribution of pressure applied to each of the feet of user is generated, a center line CL2 of the image data set is extracted, as shown in FIG. 12. The center line CL2 is extracted as the longest major axis passing through the image data set 222. As previously described, the center line CL2 may be extracted using a RANSAC algorithm. The center line CL2 will be referred to as a second center line.

When the first center line CL1 and the second center line CL2 are extracted, as described above, the position change tracker of the controller of the present invention extracts an intersection point at which the first center line CL1 and the second center line CL2 intersect as a center of rotation Pr, as shown in (a) of FIG. 13.

In addition, the position change tracker rotates the reference region 412 about the extracted center of rotation Pr toward the second center line CL2. At this time, the position change tracker rotates the reference region 412 by a predetermined angle. For example, in the case in which the predetermined angle is 1 degree, the position change tracker rotates the reference region 412 about the center of rotation Pr by 1 degree.

The position change tracker rotates the reference region until the changed pressure distribution information 321 is entirely included in the reference region 412, which is rotated about the center of rotation Pr, as described above. (b) of FIG. 13 is a view showing the state in which the rotation of the reference region is completed as the pressure distribution information 321 is entirely included in the reference region. Reference numeral 414 indicates the reference region in the state in which the rotation of the reference region is completed.

After the rotation of the reference region is completed, as described above, the position change tracker displays a foot image 244 corresponding to the reference region 414 in the state in which the rotation of the reference region is completed and the pressure distribution information 321 in an overlapping fashion, whereby the foot position change tracking is completed. FIG. 14 is a view showing the state in which the foot image is displayed so as to coincide with the foot position changed through the above process.

In FIG. 13, the reference region is rotated. Of course, the reference region and the foot image may be rotated simultaneously. However, it is preferable to rotate only the reference region, since the load applied to the controller for data processing is greatly reduced.

According to the above manner in which the changed foot position is tracked, when a pressure distribution deviating from the reference region is present, the reference region is rotated about the intersection point of the two center lines to track the foot position. Alternatively, the reference region may be moved and may then be rotated in order to track the foot position.

For example, in the above manner, the two center lines are extracted and the intersection point thereof is extracted based on the distribution of pressure applied to each of the feet of user. Alternatively, the reference region may be moved in the horizontal direction and in the vertical direction and may then be rotated depending on the position of the extracted intersection point.

An example of tracking and displaying the position of each of the feet depending on the movement of each of the feet from when the foot image is mapped at the initial stage in the above manner is shown in FIG. 15.

FIG. 15 is a view showing the distribution of pressure applied to each foot and the change of foot position after a golf ball is hit by the head of a golf club when the user takes a golf swing using the foot image mapping process and the foot position change tracking process described above.

As shown in FIG. 15, the change in distribution of pressure applied to the left foot of the user and the change in position of the left foot of the user are tracked and displayed through state (b), state (c), state (d), and state (e) until a finish is made after an impact is made in state (a).

Referring to FIG. 15, the distribution of pressure applied to the foot of the user is changed in the order of 311→321→331→341→351 according to the user's action, and the foot image is changed in the order of 234→244→254→264→274 in response to the change in position of the foot of the user. Consequently, it is possible to very intuitively recognize the portion of the foot to which the pressure is applied.

In the case in which the position of the foot of the user is changed with the result that the foot image is displayed in the state of being rotated, as shown in (c) to (e) of FIG. 15, it is preferable to further display the initial position of the foot, i.e. a region 235 corresponding to the foot image when the foot image is mapped, since the user can very intuitively recognize how his/her foot has been moved since the beginning.

Meanwhile, FIG. 16 is a view showing an example of information regarding the change in weight shift of the user, which is analyzed and displayed by the athletic posture analysis device according to the embodiment of the present invention.

(a) of FIG. 16 is a view showing the distribution of pressure applied to the two feet of the user when the user takes an address posture for a golf swing, (b) of FIG. 16 is a view showing the distribution of pressure applied to the two feet of the user when the user takes a back swing posture, (c) of FIG. 16 is a view showing the distribution of pressure applied to the two feet of the user when the user takes an impact posture, and (d) of FIG. 16 is a view showing the distribution of pressure applied to the two feet of the user when the user takes a finish posture.

Referring to (a) to (d) of FIG. 16, it can be seen that it is possible to more intuitively recognize the change in weight shift of the user according to the golf swing action than when only the distribution of pressure applied to the two feet of the user is disposed without displaying the foot image.

MODE FOR INVENTION

Various embodiments have been described in the best mode for carrying out the invention.

INDUSTRIAL APPLICABILITY

The athletic posture analysis device and the method of generating athletic posture analysis information according to the present invention are applicable to sports-related industries for analyzing athletic postures, such as golf swings, and to learning and training-related industries for analyzing sports actions, performing information processing, and using the results thereof.

The invention claimed is:

1. A golf swing posture analysis device for analyzing a golf swing posture taken by a user who stands on a foot plate, the golf swing posture analysis device comprising:
a pressure sensor plate provided at the foot plate, the pressure sensor plate having a plurality of pressure sensors configured to measure a distribution of pressure applied to each of feet of the user, who performs a golf swing, by a weight of the user;
a display configured to display golf swing posture analysis information of the user; and
a controller including a mapping processor and a tracking processor,
wherein the mapping processor is configured to:
specify a size and position of each of the feet of the user using data indicating the pressure applied to each of the feet of the user based on information measured by the pressure sensor plate; and
map a foot image having a predetermined design corresponding to the specific size of each of the feet,
wherein the tracking processor is configured to:
track the position of each of the feet when the distribution of pressure applied to each of the feet of the user is changed according to the user's golf swing by setting a reference region so as to include the foot image mapped by the mapping processor and moving the reference region such that data indicating the changed distribution of pressure applied to each of the feet of the user is included in the reference region; and
display the foot image so as to correspond to the reference region, thereby tracking the change in position of each of the feet of the user and displaying the foot image.

2. The golf swing posture analysis device according to claim 1, wherein the mapping processor comprises:
an image data generator for generating data of an image indicating the distribution of pressure applied to each of the feet of the user, measured by the pressure sensor plate;
an image data analyzer configured to analyze the image data to specify information regarding the size and the position of each of the feet of the user; and
a foot image mapping unit configured to map a predetermined foot image so as to coincide with the size and the position of each of the feet of the user, specified by the image data analyzer.

3. The golf swing posture analysis device according to claim 2, wherein the tracking processor comprises:
a position change detector configured to set the reference region so as to include the foot image mapped by the foot image mapping unit and to detect a portion of each of the feet of the user at which the distribution of pressure applied to each of the feet of the user deviates from the reference region when the distribution of pressure applied to each of the feet of the user is changed according to the user's action; and
a position change tracker for calculating a center of rotation using data indicating the changed distribution of pressure applied to each of the feet of the user when information regarding the distribution of pressure applied to each of the feet of the user that deviates from the reference region is present, rotating the reference region about the center of rotation until the data indicating the changed distribution of pressure applied to each of the feet of the user are included in the reference region, and displaying the foot image so as to correspond to the rotated reference region.

4. The golf swing posture analysis device according to claim 3, wherein the position change tracker is configured to extract a longest major axis passing through the mapped foot image as a first center line, to extract a longest major axis passing through an image data set indicating the distribution of pressure applied to each of the feet of the user in a state of deviating from the reference region as a second center line, to extract an intersection point of the first center line and the second center line as the center of rotation, and to rotate the reference region about the extracted center of rotation until information regarding the distribution of pressure applied to each of the feet of the user or image data indicating the distribution of pressure applied to each of the feet of the user in the state of deviating from the reference region are included in the reference region.

5. A method of analyzing a golf swing posture taken by a user who stands on a foot plate to generate golf swing posture analysis information, the method comprising:
specifying a size and position of each of feet of the user using information regarding a distribution of pressure applied to each of the feet of the user by a weight of the user, measured by a pressure sensor plate provided at the foot plate for measuring a distribution of pressure applied to each of the feet of the user, who performs a golf swing, by the weight of the user and mapping a predetermined foot image;
displaying the mapped foot image and the information regarding the distribution of pressure applied to each of the feet of the user, measured by the pressure sensor plate, in an overlapping fashion; and
tracking a position of each of the feet of the user changed according to the user's golf swing and displaying the foot image so as to correspond to the tracked position of each of the feet of the user, wherein the step of displaying the foot image so as to correspond to the tracked position of each of the feet of the user comprises:
setting a reference region so as to include the mapped foot image;
moving the reference region such that, when the distribution of pressure applied to each of the feet of the user is changed according to the user's action, data indicating the changed distribution of pressure applied to each of the feet of the user is included in the reference region; and
displaying the foot image so as to correspond to the reference region, thereby tracking the change in position of each of the feet of the user and displaying the foot image.

6. The method according to claim 5, wherein the step of mapping the foot image comprises:
generating image data indicating the distribution of pressure applied to each of the feet of the user, measured by the pressure sensor plate;
analyzing the image data to specify information regarding the size and position of each of the feet of the user;
determining a size of the predetermined foot image based on information regarding the specified size of each of the feet of the user; and mapping the foot image having the determined size so as to coincide with the information regarding the specified position of each of the feet of the user.

7. The method according to claim 5, wherein the step of displaying the foot image so as to correspond to the tracked position of each of the feet of the user comprises:
   setting the reference region so as to include the mapped foot image;
   detecting a portion of each of the feet of the user at which the distribution of pressure applied to each of the feet of the user deviates from the reference region when the distribution of pressure applied to each of the feet of the user is changed according to the user's action;
   calculating a center of rotation using data indicating the changed distribution of pressure applied to each of the feet of the user when the information regarding the distribution of pressure applied to each of the feet of the user that deviates from the reference region is present,
   rotating the reference region about the center of rotation until the data indicating the changed distribution of pressure applied to each of the feet of the user are included in the reference region; and
   displaying the foot image so as to correspond to the rotated reference region.

8. The method according to claim 6, wherein the step of displaying the foot image so as to correspond to the tracked position of each of the feet of the user comprises:
   setting the reference region so as to include the mapped foot image;
   extracting a longest major axis passing through the mapped foot image as a first center line;
   extracting a longest major axis passing through an image data set indicating the distribution of pressure applied to each of the feet of the user in a state of deviating from the reference region as a second center line;
   extracting an intersection point of the first center line and the second center line as a center of rotation;
   rotating the reference region about the center of rotation; and
   stopping the rotation of the reference region when the image data set indicating the distribution of pressure applied to each of the feet of the user in the state of deviating from the reference region is included in the reference region, rotated about the center of rotation, and displaying the foot image so as to correspond to the rotated reference region.

9. The method according to claim 5, wherein the step of displaying the foot image so as to correspond to the tracked position of each of the feet of the user comprises displaying the foot image so as to correspond to the tracked position of each of the feet of the user in a state in which a region corresponding to the foot image mapped at the step of mapping the foot image is displayed.

* * * * *